(12) United States Patent
Song et al.

(10) Patent No.: US 9,782,461 B2
(45) Date of Patent: Oct. 10, 2017

(54) HUMAN COAGULATION FACTOR LIGHT CHAIN PROTEIN AND USE OF THE SAME

(71) Applicant: CHENGDU SOURCEBIO LIMITED-LIABILITY COMPANY, Chengdu (CN)

(72) Inventors: Xu Song, Sichuan (CN); Ling Li, Sichuan (CN); Jinwu Chen, Sichuan (CN); Dongsheng Liao, Sichuan (CN); Dengjiao Ma, Sichuan (CN)

(73) Assignee: Chengdu Sourcebio Limited-Liability Company, Chengdu (CN)

( * ) Notice: Subject to any disclaimer, the term of this patent is extended or adjusted under 35 U.S.C. 154(b) by 0 days.

(21) Appl. No.: 14/894,415

(22) PCT Filed: May 22, 2014

(86) PCT No.: PCT/CN2014/078108
§ 371 (c)(1),
(2) Date: Nov. 27, 2015

(87) PCT Pub. No.: WO2014/190871
PCT Pub. Date: Dec. 4, 2014

(65) Prior Publication Data
US 2016/0106818 A1 Apr. 21, 2016

(30) Foreign Application Priority Data

May 29, 2013 (CN) .......................... 2013 1 0206823

(51) Int. Cl.
*A61K 38/36* (2006.01)
*A61K 38/48* (2006.01)
*C07K 14/745* (2006.01)
*A61K 38/00* (2006.01)

(52) U.S. Cl.
CPC ........ *A61K 38/4846* (2013.01); *C07K 14/745* (2013.01); *A61K 38/00* (2013.01); *C12Y 304/21006* (2013.01); *C12Y 304/21021* (2013.01); *C12Y 304/21022* (2013.01)

(58) Field of Classification Search
CPC .................................................... A61K 38/36
See application file for complete search history.

(56) References Cited

FOREIGN PATENT DOCUMENTS

| CN | 103079588 | 5/2013 |
| CN | 103079588 A | 5/2013 |

OTHER PUBLICATIONS 2. coagulation factor IX, partial [Homo sapiens], GenBank: AAA51981.1, Nov. 1, 1994.
1. Chain L, Dissecting and Designing Inhibitor Selectivity Determinants At the S1 Site Using An Artificial Ala190 Protease (Ala190 Upa) PDB: 1O5D_L, Oct. 10, 2012.
factor X prepeptide, partial [Homo sapiens], GenBank: AAA52490. 1, Nov. 8, 1994.
Office Action from Chinese Application No. 201310206823.5 dated May 4, 2016.
R. Lee West et al., "Blood Coagulation Factor Activity in Experimental Endotoxemia," Annals of Surgery, Apr. 1966, 163(4), pp. 567-572.
Predicted: coagulation factor X [Gorilla gorilla gorilla], GenBank: XP_004054811.1 Dec. 3, 2012.
Jing Li, "Clinical significance of coagulation system in bacterial infectious diseases," China Academic Journal Electronic Publishing House, May 2008, pp. 384-385.

*Primary Examiner* — Maryam Monshipouri
(74) *Attorney, Agent, or Firm* — Calfee, Halter & Griswold LLP

(57) ABSTRACT

In the invention, the minimum inhibitory concentrations of human coagulation factor light-chain proteins against different Gram-negative bacteria are detected with the in vitro antibacterial activity and the inhibiting effect of the human coagulation factor light-chain proteins against different Gram-negative bacteria is detected with the in vivo antibacterial activity. It has been shown that human coagulation factor light-chain proteins have an obvious inhibitory effect on the Gram-negative bacteria, so as to develop a novel class of medicaments for treating Gram-negative bacteria infection. It has been demonstrated by mass spectrometry and silver staining that human coagulation factor light-chain proteins have the effect on hydrolyzing and eliminating the endotoxin, which facilitates the development of a novel class of medicaments for treating endotoxemia. The human coagulation factor light-chain proteins are light chain proteins of human coagulation factors VII, IX, and X, as well as a protein having homology of more than 50% thereof.

14 Claims, 9 Drawing Sheets

HUMAN COAGULATION FACTOR LIGHT CHAIN PROTEIN AND USE OF THE SAME

CROSS REFERENCE TO RELATED APPLICATIONS

This application is the U.S. national phase entry of PCT/CN2014/078108, with an international filing date of May 22, 2014, which claims priority to and any benefit of Chinese Patent Application No. 201310206823.5 filed May 29, 2013, the entire contents of which are incorporated by reference in their entirety.

SEQUENCE LISTING

The instant application contains a Sequence Listing which is being submitted in ASCII format via EFS-Web and is hereby incorporated by reference in its entirety. Said ASCII copy is named Amended sequence listing for national phase (WO2014190871).txt and is 10 kilobytes in size.

TECHNICAL FIELD

The present invention belongs to biomedical field, and especially relates to a human coagulation factor light chain protein and use thereof in the pharmaceutical industry.

BACKGROUND

Gram-negative bacteria refer broadly to the bacteria which are stained in red in Gram's staining reaction, and they are different from the Gram-positive bacteria during the Gram's staining due to the difference in the structure of the cell wall (the positive bacteria being stained in violet). The Gram-negative bacteria are represented by *Escherichia coli*, as well as Proteus, *Shigella dysenteriae, Klebsiella pneumoniae, Brucella bacilli, Haemophilus influenzae, Haemophilus parainfluenzae, Moraxella catarrhalis*, Acinetobacter and so on. Pathogenicity of such bacteria is often associated with a particular component in their cell walls, lipopolysaccharide (also known as endotoxin). In human's body, lipopolysaccharide will induce the body to produce a large amount of cytokines and to activate the immune system, eventually evoking innate immune responses against the pathogenic bacteria within the body. For instance, redness and swelling are the results of generation and release of a large amount of cytokines.

In addition to eliminating the focus of infection and symptomatic and supportive treatment, antibiotics also need to be used during the treatment of a Gram-negative bacteria infection. At present, the antibiotics mainly used are aminoglycosides, beta-lactams, etc. These antibiotics have potent bactericidal effects on various Gram-negative bacteria, and moreover exhibit longer post-antibiotic effects on the common Gram-negative bacilli such as *Pseudomonas aeruginosa, Klebsiella pneumonia*, and *E. coli*. In addition to the antibiotics, the agents such as prostaglandin synthetase inhibitor, levamisole, and tuftsin are also useful in treatment of the Gram-negative bacteria infection. However, with the extensive application of antibiotics, the abuse of antibiotics in clinical medicine results in progression of the drug resistance of bacteria from single drug resistance into multi drug resistance, thus making many second-line antibiotics which would have been used effectively as alternatives ineffective. Secondly, the antibacterial drug may induce the generation of endotoxin while killing/inhibiting the bacteria, which increases the difficulty of treating the disease. Thus, while novel antibiotics with potent killing effect come out continuously and advanced supportive therapies occurs, treatment of the endotoxemia caused by Gram's negative bacteria infection is still a challenge in the clinical scenario, particularly with an unacceptable mortality rate of 20-30%. It has been reported that lipopolysaccharide is the major pathogenic factor which leads to a series of toxicity reaction occurring after the Gram-negative bacteria infection. Although antibiotics have a better effect of eliminating the bacteria, they have no effect on the lipopolysaccharide free in the blood and a wide variety of detrimental cytokines produced by target cells which are persistently stimulated with the free lipopolysaccharide. Therefore, when choosing an antibacterial drug clinically, a comprehensive consideration should be taken for the result of drug sensitive test and the feature of inducing release of the endotoxin. Thirdly, since lipopolysaccharide is located on the surface of the cell wall of Gram-negative bacteria, many early types of antibiotics are unable to inhibit such bacteria effectively. Based on these reasons, novel fields are being explored actively in treating Gram-negative bacteria infection in the recent years.

Antimicrobial peptides (AMPs) refer to short peptides having antibacterial activities, most of which have thermal stability, high alkalinity and broad-spectrum anti-bacterial activities. Currently, about more than 2000 of AMPs have already been identified from various organisms. These AMPs are synthesized after induction, play an important role in an organism's resistance against the invasion of a pathogen, and are considered an important defensive constituent for the non-specific immunological function in an organism. Accordingly, it becomes a hot spot and a challenge to find out novel APMs against Gram-negative bacteria.

Human coagulation factor VII (human factor VII, hFVII) is a naturally-occurring protein in the human's body with a molecular weight of about 50 kD. Its molecule comprises four domains: a membrane-bound N-terminal γ-carboxyglutamic acid domain (Gla domain), two epidermal growth factor-like domains (EGF1 and EGF2), and a C-terminal serine protease domain. It also has several analogues with higher sequence homology in the human body, such as human coagulation factor IX (human factor IX, hFIX), human coagulation factor X (human factor X, hFX), etc. Up to now, there is no relevant report on treatment of a bacteria infection with the light chains from the human coagulation factors VII, IX, X as antibacterial agents and no report on preparation of a medicament for treating endotoxemia caused by a Gram-negative bacterium.

SUMMARY OF THE INVENTION

One of the objectives of the present invention is to provide an artificially-prepared human coagulation factor light chain protein. Another objective of the present invention is to prove that the human coagulation factor light chain protein has an inhibitory effect on the Gram-negative bacteria, so as to develop a novel class of medicaments for treating Gram-negative bacteria infection and medicaments for treating endotoxemia caused by Gram-negative bacteria.

Set forth in the present invention is a protein encoded by a human coagulation factor light chain gene, the amino acid sequence thereof being described in SEQ ID NO: 1 in the sequence listing, or a protein having homology of more than 50% to the amino acid sequence described in SEQ ID NO: 1. The amino acid sequence of the protein having homology of more than 50% to the amino acid sequence described in SEQ ID NO: 1 is set forth in SEQ ID NO: 2 or SEQ ID NO: 3 in the sequence listing.

Alternatively, set forth in the present invention is a protein encoded by a human coagulation factor light chain gene, the amino acid sequence thereof being described in SEQ ID NO: 2 in the sequence listing, or a protein having homology of more than 50% to the amino acid sequence described in SEQ ID NO: 2. The amino acid sequence of the protein having homology of more than 50% to the amino acid sequence described in SEQ ID NO: 2 is set forth in SEQ ID NO: 1 or SEQ ID NO: 3 in the sequence listing.

Alternatively, set forth in the present invention is a protein encoded by a human coagulation factor light chain gene, the amino acid sequence thereof being described in SEQ ID NO: 3 in the sequence listing, or a protein having homology of more than 50% to the amino acid sequence described in SEQ ID NO: 3. The amino acid sequence of the protein having homology of more than 50% to the amino acid sequence described in SEQ ID NO: 3 is set forth in SEQ ID NO: 1 or SEQ ID NO: 2 in the sequence listing.

The human coagulation factor light chain protein with an amino acid sequence described in SEQ ID NO: 1 in the sequence listing is designated as LhF VII. The human coagulation factor light chain protein with an amino acid sequence described in SEQ ID NO: 2 in the sequence listing is designated as LhF IX. The human coagulation factor light chain protein with an amino acid sequence described in SEQ ID NO: 3 in the sequence listing is designated as LhF X.

The above-mentioned proteins encoded by the human coagulation factor light chain genes are expressed from a prokaryotic recombinant plasmid, expressed from a eukaryotic recombinant plasmid, or prepared by chemical synthesis.

The recombinant prokaryotic or eukaryotic plasmid for the human coagulation factor light chain proteins set forth in the present invention is respectively constructed by the nucleotide sequence described in SEQ ID NO: 4 in the sequence listing or a gene having homology of more than 50% to the nucleotide sequence described in SEQ ID NO: 4 in the sequence listing in combination with a prokaryotic or eukaryotic vector. The nucleotide sequence of the gene having homology of more than 50% to the nucleotide sequence described in SEQ ID NO: 4 is set forth in SEQ ID NO: 5 or SEQ ID NO: 6 in the sequence listing. The prokaryotic vector is the pET plasmid system, including pET-14b, pET-19b, pET-21a (+), pET-28a (+), and pET-42a (+); and the eukaryotic vector is pcDNA3.1 (+) and pcDNA3.1 (−).

The recombinant prokaryotic or eukaryotic plasmid for the human coagulation factor light chain proteins set forth in the present invention is respectively constructed by the nucleotide sequence described in SEQ ID NO: 5 in the sequence listing or a gene having homology of more than 50% to the nucleotide sequence described in SEQ ID NO: 5 in the sequence listing in combination with a prokaryotic or eukaryotic vector. The nucleotide sequence of the gene having homology of more than 50% to the nucleotide sequence described in SEQ ID NO: 5 is set forth in SEQ ID NO: 4 or SEQ ID NO: 6 in the sequence listing. The prokaryotic vector is the pET plasmid system, including pET-14b, pET-19b, pET-21a (+), pET-28a (+), and pET-42a (+); and the eukaryotic vector is pcDNA3.1 (+) and pcDNA3.1 (−).

The recombinant prokaryotic or eukaryotic plasmid for the human coagulation factor light chain proteins set forth in the present invention is respectively constructed by the nucleotide sequence described in SEQ ID NO: 6 in the sequence listing or a gene having homology of more than 50% to the nucleotide sequence described in SEQ ID NO: 6 in the sequence listing in combination with a prokaryotic or eukaryotic vector. The nucleotide sequence of the gene having homology of more than 50% to the nucleotide sequence described in SEQ ID NO: 6 is set forth in SEQ ID NO: 4 or SEQ ID NO: 5 in the sequence listing. The prokaryotic vector is the pET plasmid system, including pET-14b, pET-19b, pET-21a (+), pET-28a (+), and pET-42a (+); and the eukaryotic vector is pcDNA3.1 (+) and pcDNA3.1 (−).

The steps used in the present invention are as follows:

(1) the genes encoding the recombinant proteins LhF VII, LhF IX, and LhF X or the genes having homology of more than 50% thereto are obtained by a PCR reaction;

(2) the individual gene fragments amplified above are inserted respectively into the prokaryotic or eukaryotic vector to construct the recombinant prokaryotic or eukaryotic plasmid, followed by transformation of the resultant recombinant prokaryotic or eukaryotic plasmid into competent bacteria to be cultured, and then the recombinant plasmid comprising the correctly inserted fragments are screened by sequencing;

(3) the recombinant prokaryotic plasmid with the correct sequencing result is transformed into an engineering bacterium to be expressed; isolation and purification of the expressed proteins to obtain the recombinant proteins LhF VII, LhF IX, and LhF X or the proteins having homology of more than 50% thereto; or the resultant recombinant eukaryotic plasmid is transfected into mammalian cells to be cultured, a stable cell line is established for eukaryotic expression, then isolation and purification of the expressed protein to obtain the recombinant proteins LhF VII, LhF IX, and LhF X or the proteins having homology of more than 50% thereto;

(4) the in vitro antibacterial activities of the recombinant proteins LhF VII, LhF IX, and LhF X or the proteins having homology of more than 50% thereto are assayed;

(5) the in vivo antibacterial activities of the recombinant proteins LhF VII, LhF IX, and LhF X or the proteins having homology of more than 50% thereto are assayed;

(6) the hydrolysis of the lipopolysaccharide by the recombinant proteins LhF VII, LhF IX, and LhF X or the proteins having homology of more than 50% thereto is subjected to mass spectrometric detection;

(7) the hydrolysis of the lipopolysaccharide by the recombinant proteins LhF VII, LhF IX, and LhF X or the proteins having homology of more than 50% thereto is subjected to silver staining detection;

The prokaryotic vector is the pET plasmid system which includes the prokaryotic expression plasmids such as pET-14b, pET-19b, pET-21a (+), pET-28a (+), pET-42a (+), etc; and the eukaryotic vector is pcDNA3.1 (+), pcDNA3.1 (−), etc.

Chemical synthesis of the human coagulation factor light chain protein is usually outsourced to professional companies.

The proteins LhF VII, LhF IX, and LhF X set forth in the present invention are able to hydrolyze the lipopolysaccharide of Gram-negative bacteria (also known as endotoxin, a major component in the outer-membrane of a Gram negative bacterium) and disrupt the stability of cellular structure, thereby exerting the bactericidal action. Meanwhile, it has been shown that the light chain proteins have very strong binding to the tissue factor. When the body is injured, the tissue factor will be exposed at the wound in a large amount, which allows the light chain proteins to aggregate accordingly at the wound, exerting a targeted bacteriostatic effect. Assay on the in vitro activity inhibiting the Gram-negative bacteria shows that: the proteins LhF VII, LhF IX, and LhF X have a significant inhibitory effect on the Gram-negative bacteria. The minimum inhibitory concentrations (MICs) of the proteins for *E. coli* DH5α, *E. coli* BL21, *Pseudomonas aeruginosa, Klebsiella pneumonia, Enterobacter cloacae, Aeromonas hydrophila, Citrobacter diversus, Moraxella catarrhalis, Proteus mirabilis, Proteus vulgaris, Serratia marcescens* are as follows:

| Strain | MIC (µg/mL) | | |
| --- | --- | --- | --- |
| | LhF VII | LhF IX | LhF X |
| *E. coli* DH5α | 25 | 25 | 25 |
| *E. coli* BL21 | 50 | 50 | 50 |
| *Pseudomonas aeruginosa* | 25 | 25 | 25 |
| *Klebsiella pneumonia* | 25 | 25 | 25 |
| *Enterobacter cloacae* | 25 | 50 | 50 |
| *Aeromonas hydrophila* | 25 | 25 | 25 |
| *Citrobacter diversus* | 50 | 50 | 25 |
| *Moraxella catarrhalis* | 25 | 25 | 25 |
| *Proteus mirabilis* | 25 | 25 | 25 |
| *Proteus vulgaris* | 50 | 50 | 25 |
| *Serratia marcescens* | 25 | 50 | 25 |

Assays on the in vivo antibacterial activity of the proteins LhF VII, LhF IX, and LhF X shows that: the proteins LhF VII, LhF IX, and LhF X have a significant inhibitory effect on the Gram-negative bacteria in animals and can keep the mice infected with a lethal dose of *Pseudomonas aeruginosa* at a survival rate of 100% for 14 days. Moreover, all of the mice not infected with *Pseudomonas aeruginosa* survived after injecting with the proteins, demonstrating that the proteins LhF VII, LhF IX, and LhF X set forth in the present invention (themselves) have low immunogenicity and low toxicity.

Since the proteins LhF VII, LhF IX, and LhF X set forth in the present invention can hydrolyze the lipopolysaccharide of Gram-negative bacteria (also known as endotoxin, seen in Examples 12 and 13) and lipopolysaccharide is the major pathogenic factor causing endotoxemia, these proteins can be used in preparing a medicament for treating endotoxemia caused by the Gram-negative bacteria.

The present invention has the following advantageous effects:

1. The artificially-prepared human coagulation factor light chain proteins provided in the present invention are able to hydrolyze the outer membrane of the Gram-negative bacteria, disrupt the stability of cellular structure, and have significant inhibitory effects on the Gram-negative bacteria, thereby providing a novel class of therapeutic drugs for treating diseases caused by the Gram-negative bacteria infection.

2. The artificially-prepared human coagulation factor light chain proteins provided in the present invention are able to hydrolyze the lipopolysaccharide (also known as endotoxin) of the Gram-negative bacteria, thereby providing a novel class of therapeutic drugs for treating endotoxemia caused by the Gram-negative bacteria.

3. The artificially-prepared human coagulation factor light chain proteins provided in the present invention can exhibit an excellent targeted bactericidal effect on Gram negative bacteria at the wound site by targeted localization at the wound site via binding to tissue factor, and be prospective to be used in preparation of a novel targeted antibacterial drug.

4. The light chain proteins of human coagulation factors VII, IX, and X are natural and intrinsic components in the human body, and use of the light chain proteins as the bacteriostatic domain in the present invention can reduce the immunogenicity of the medicament effectively.

5. Since the recombination human coagulation factor light chain protein could be expressed properly in the cells of *E. coli* directly through the genetic engineering techniques, the production cost is lower, suitable for industrial production.

BRIEF DESCRIPTION OF ACCOMPANYING DRAWINGS

Figure 7:
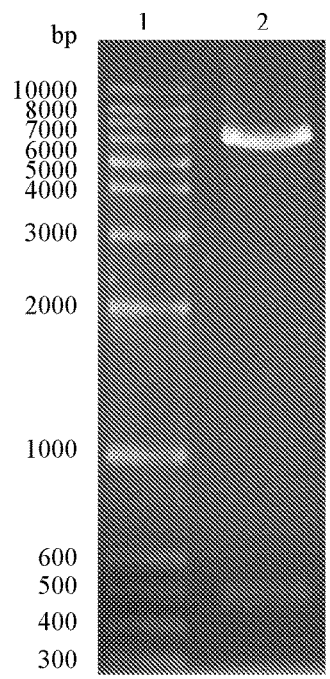

FIG. 7 is the electrophoregram for identification of the restriction-endonuclease digested fragments of the recombinant plasmid pET19blhf VII in Example 4, wherein Lane 1 is the DNA molecular weight marker (Marker 1+1 kb Marker, purchased from TIANGEN BIOTECH Co. Ltd.) and Lane 2 is the pET19b vector fragment and the DNA fragment encoding the recombinant protein LhF VII which are obtained after restriction-endonuclease double digestion of the recombinant plasmid pET19blhf VII.

Figure 8:
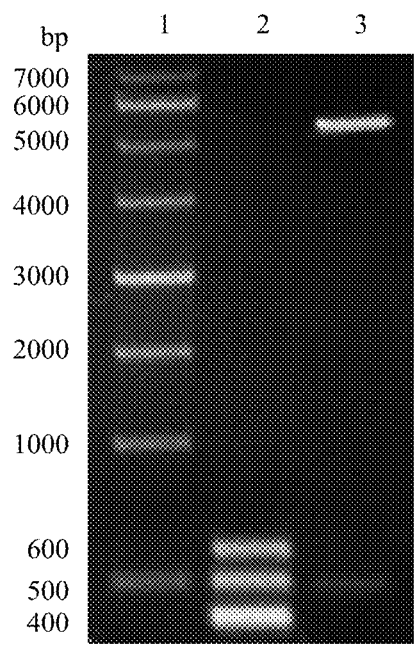

FIG. 8 is the electrophoregram for identification of the restriction-endonuclease digested fragments of the recombinant plasmid pET19blhf IX in Example 4, wherein Lane 1 is the DNA molecular weight marker (1 kb Marker, purchased from TIANGEN BIOTECH Co. Ltd.); Lane 2 is the DNA molecular weight marker (Marker I, purchased from TIANGEN BIOTECH Co. Ltd.); and Lane 3 is the pET19b vector fragment and the DNA fragment encoding the recombinant protein LhF IX which are obtained after restriction-endonuclease double digestion of the recombinant plasmid pET19blhf IX.

Figure 9:
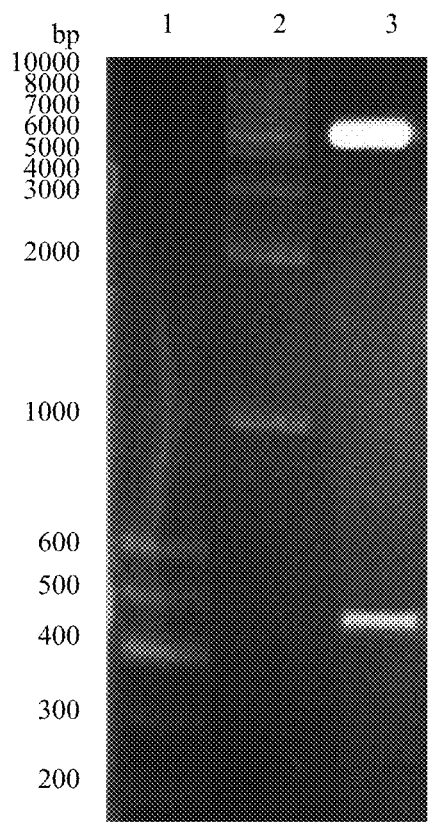

FIG. 9 is the electrophoregram for identification of the restriction-endonuclease digested fragments of the recombinant plasmid pET19blhf X in Example 4, wherein Lane 1 is the DNA molecular weight marker (Marker 1, purchased from TIANGEN BIOTECH Co. Ltd.); Lane 2 is the DNA molecular weight marker (1 kb Marker, purchased from TIANGEN BIOTECH Co. Ltd.); and Lane 3 is the pET19b vector fragment and the DNA fragment encoding the recombinant protein LhF X which are obtained after restriction-endonuclease double digestion of the recombinant plasmid pET19blhf X.

Figure 10:
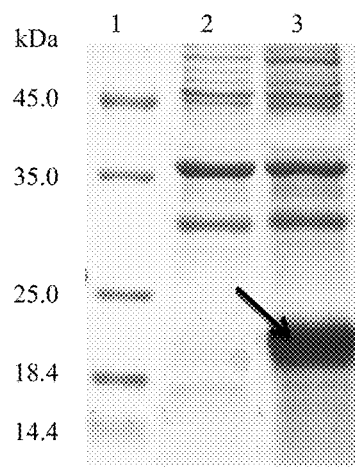

FIG. 10 is the SDS-PAGE analysis of inducible expression of the recombinant protein LhF VII from the recombinant plasmid pET19blhf VII in E. coli in Example 5, wherein Lane 1 is the protein molecular weight marker (Unst. Protein Marker, purchased from Thermo Scientific); Lane 2 is the total protein of the E. coli without expressing the recombinant protein LhF VII before induction; and Lane 3 is the total protein of the E. coli after expressing the recombinant protein LhF VII by induction, the arrowhead indicating the expressed recombinant protein LhF VII.

Figure 11:
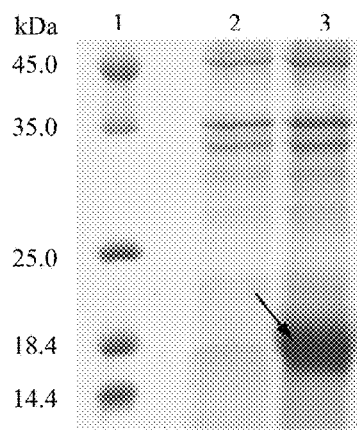

FIG. 11 is the SDS-PAGE analysis of inducible expression of the recombinant protein LhF IX from the recombinant plasmid pET19blhf IX in E. coli in Example 5, wherein Lane 1 is the protein molecular weight marker (Unst. Protein Marker, purchased from Thermo Scientific); Lane 2 is the total protein of the E. coli without expressing the recombinant protein LhF IX before induction; and Lane 3 is the total protein of the E. coli after expressing the recombinant protein LhF IX by induction, the arrowhead indicating the expressed recombinant protein LhF IX.

Figure 12:
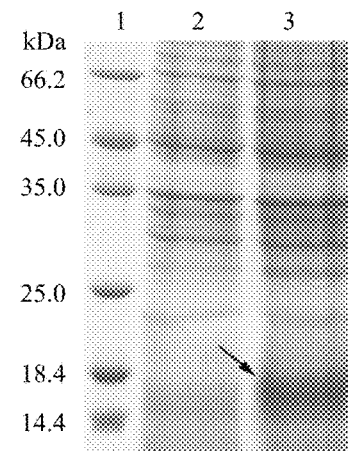

FIG. 12 is the SDS-PAGE analysis of inducible expression of the recombinant protein LhF X from the recombinant plasmid pET19blhf X in E. coli in Example 5, wherein Lane 1 is the protein molecular weight marker (Unst. Protein Marker, purchased from Thermo Scientific); Lane 2 is the total protein of the E. coli without expressing the recombinant protein LhF X before induction; and Lane 3 is the total protein of the E. coli after expressing the recombinant protein LhF X by induction, the arrowhead indicating the expressed recombinant protein LhF X.

Figure 13:
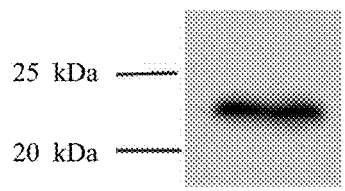

FIG. 13 is the Western-blot analysis for identification of the recombinant protein LhF VII by inducible expression in Example 5.

Figure 14:
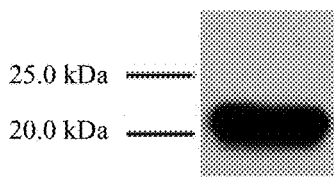

FIG. 14 is the Western-blot analysis for identification of the recombinant protein LhF IX by inducible expression in Example 5.

Figure 15:
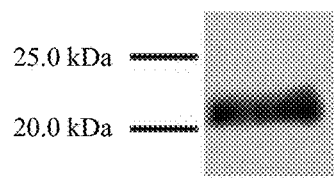

FIG. 15 is the Western-blot analysis for identification of the recombinant protein LhF X by inducible expression in Example 5.

Figure 16:
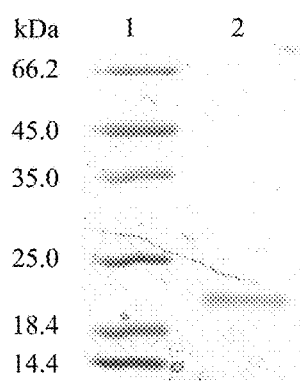

FIG. 16 is the SDS-PAGE analysis for identification of the recombinant protein LhF VII purified by affinity chromatography in Example 6, wherein Lane 1 is the protein molecular weight marker (Unst. Protein Marker, purchased from Thermo Scientific) and Lane 2 is the recombinant protein LhF VII post purification.

Figure 17:
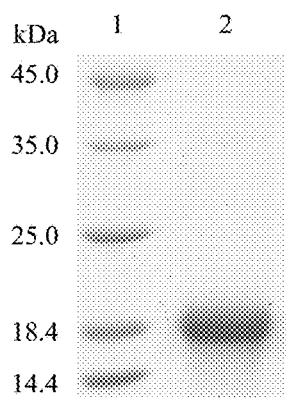

FIG. 17 is the SDS-PAGE analysis for identification of the recombinant protein LhF IX purified by affinity chromatography in Example 6, wherein Lane 1 is the protein molecular weight marker (Unst. Protein Marker, purchased from Thermo Scientific) and Lane 2 is the recombinant protein LhF IX post purification.

Figure 18:
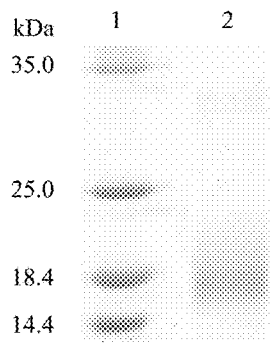

FIG. 18 is the SDS-PAGE analysis for identification of the recombinant protein LhF X purified by affinity chromatography in Example 6, wherein Lane 1 is the protein molecular weight marker (Unst. Protein Marker, purchased from Thermo Scientific) and Lane 2 is the recombinant protein LhF X post purification.

Figure 19:
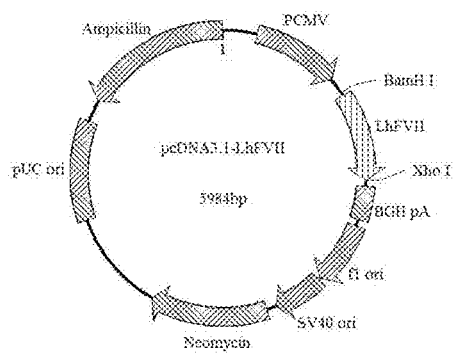

FIG. 19 is the schematic representation of the recombinant eukaryotic plasmid pcDNA3.1-LhF VII set forth in Example 7, wherein the counterclockwise sequence is the forward gene fragment and the clockwise one is the reverse gene fragment.

Figure 20:
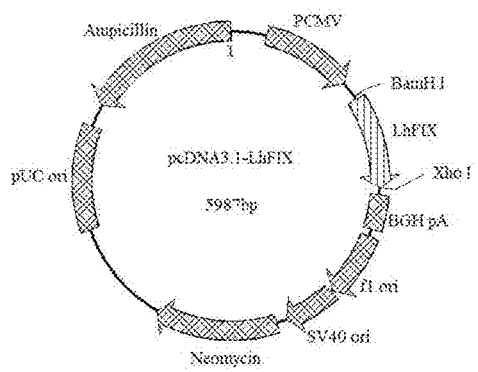

FIG. 20 is the schematic representation of the recombinant eukaryotic plasmid pcDNA3.1-LhF IX set forth in Example 7, wherein the counterclockwise sequence is the forward gene fragment and the clockwise one is the reverse gene fragment.

Figure 21:
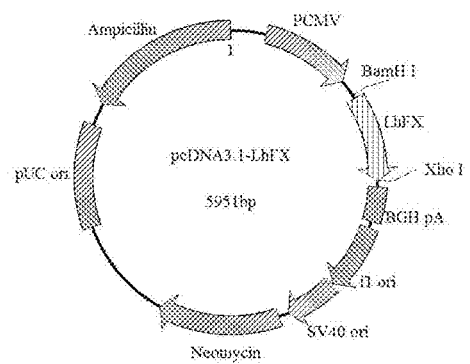

FIG. 21 is the schematic representation of the recombinant eukaryotic plasmid pcDNA3.1-LhF X set forth in Example 7, wherein the counterclockwise sequence is the forward gene fragment and the clockwise one is the reverse gene fragment.

Figure 22:
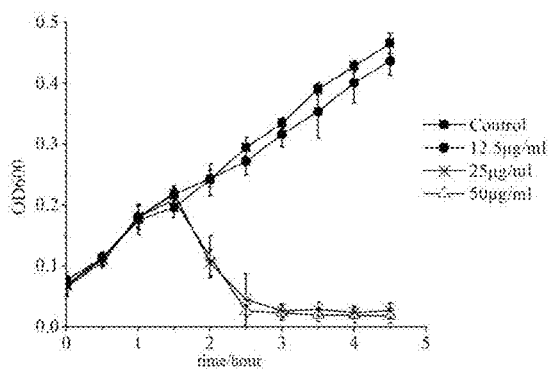

FIG. 22 is the growth curve of E. coli DH5α treated with the recombinant protein LhF VAII set forth in Example 10, in which ---■--- Control: the control group without addition of protein; ---●--- 12.5 µg/ml: the experimental group with 12.5 µg/mL of the recombinant protein LhF VII; ---▲--- 25 µg/ml: the experimental group with 25 µg/mL of the recombinant protein LhF VII; ---◇--- 50 µg/ml: the experimental group with 50 µg/mL of the recombinant protein LhF VII.

Figure 23:
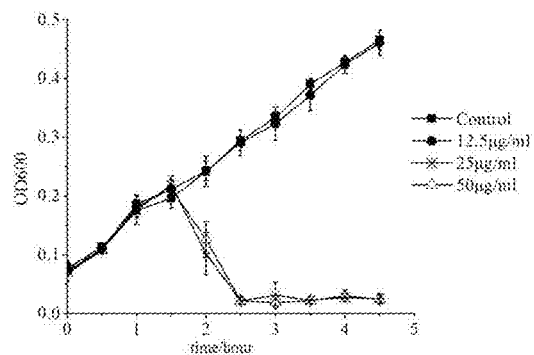

FIG. 23 is the growth curve of E. coli DH5α treated with the recombinant protein LhF IX set forth in Example 10, in which ---■--- Control: the control group without addition of protein; ---●--- 12.5 µg/ml: the experimental group with 12.5 µg/mL of the recombinant protein LhF IX; ---▲--- 25 µg/ml: the experimental group with 25 µg/mL of the recombinant protein LhF IX; ---◇--- 50 µg/ml: the experimental group with 50 µg/mL of the recombinant protein LhF IX.

Figure 24:
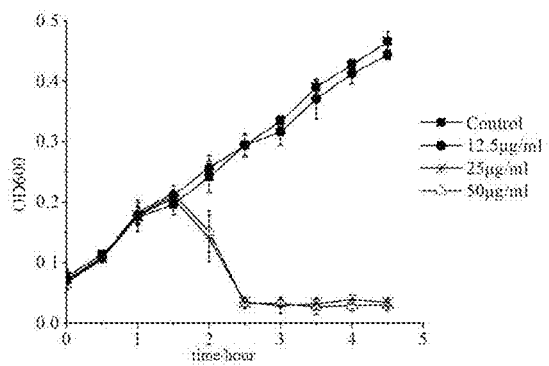

FIG. 24 is the growth curve of E. coli DH5α treated with the recombinant protein LhF X set forth in Example 10, in which ---■--- Control: the control group without addition of protein; ---●--- 12.5 µg/ml: the experimental group with 12.5 µg/mL of the recombinant protein LhF X; ---▲--- 25 µg/ml: the experimental group with 25 µg/mL of the recombinant protein LhF X; ---◇--- 50 µg/ml: the experimental group with 50 µg/mL of the recombinant protein LhF X.

Figure 25:
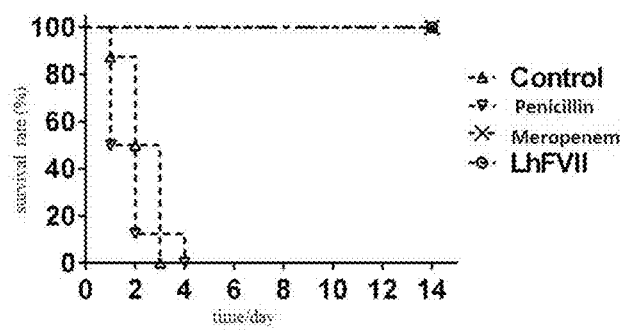

FIG. 25 is the curve showing that the recombinant protein LhF VII increases the survival rate of the mice infected a lethal dose of Pseudomonas aeruginosa as set forth in Example 11, in which ▲ Control: the infected mice with no medicament injected; ✕ meropenem: the infected mice injected with meropenem; ∇ penicillin: the infected mice injected with penicillin; ○ LhF VII: the infected mice injected with the recombinant protein LhF VII.

Figure 26:
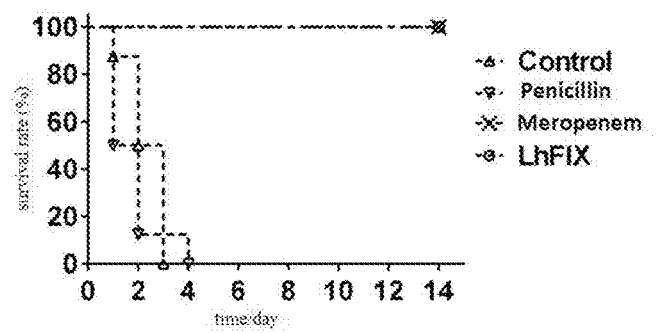

FIG. 26 is the curve showing that the recombinant protein LhF IX increases the survival rate of the mice infected with a lethal dose of Pseudomonas aeruginosa as set forth in Example 11, in which ▲ Control: the infected mice with no medicament injected; ∇ penicillin: the infected mice injected with penicillin; ✕ meropenem: the infected mice injected with meropenem; ○ LhF IX: the infected mice injected with the recombinant protein LhF IX.

Figure 27:
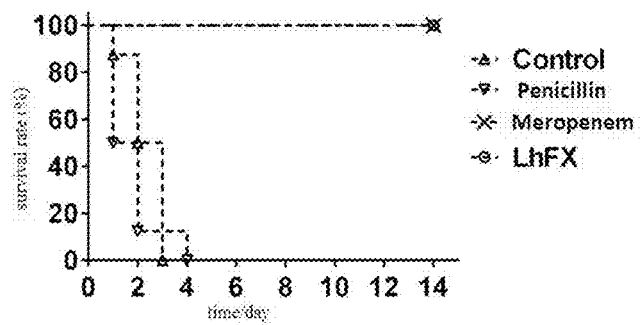

FIG. 27 is the curve showing that the recombinant protein LhF X increases the survival rate of the mice infected with a lethal dose of Pseudomonas aeruginosa as set forth in Example 11, in which ▲ Control: the infected mice with no medicament injected; ∇ penicillin: the infected mice injected with penicillin; ✕ meropenem: the infected mice injected with meropenem; ○ LhF X: the infected mice injected with the recombinant protein LhF X.

Figure 28:
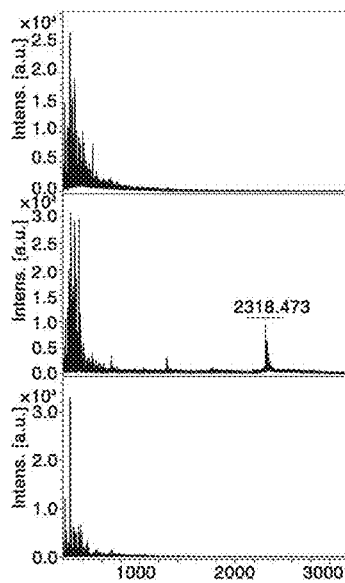

FIG. 28 is the mass spectrometric detection for hydrolysis of LPS by the recombinant protein LhF VII set forth in Example 12, wherein the top spectrum is the mass spectrum for the protein LhF VII; the middle spectrum is the mass spectrum for the untreated LPS; and the bottom spectrum is the mass spectrum after treatment of LPS with the protein LhF VII.

Figure 29:
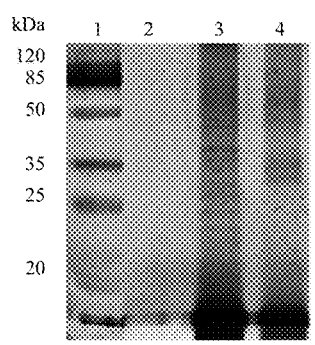

FIG. 29 is a silver staining image for hydrolysis of LPS by the recombinant protein LhF VII set forth in Example 13, in which Lane 1 is the prestained protein marker; Lane 2 is the recombinant protein LhF VII; Lane 3 is the untreated *E. coli* K12 LPS; Lane 4 is the *E. coli* K12 LPS treated with LhF VII.

DETAILED DESCRIPTION

The present invention will be further illustrated below in connection with the Examples. In the Examples described hereinafter, where the particular experiment conditions are not otherwise noted, they will follow the conventional conditions well known to the person of skill in the art, such as the conditions and experimental steps described in Molecular Cloning: A Laboratory Manual, Sambrook et al (Ed.), New York, Cold Spring Harbor Laboratory Press, 1989, An Conventional Manual for Laboratory Animals (National Center for Standard Laboratory Animals, November, 2004), and a Manual of Basic Technique, 5th Edition (John Wiley & Sons, Inc., 2005), or follow the conditions and experimental steps recommended by the manufacture.

Example 1

Obtaining the Gene Encoding the Recombination Protein LhF VII

1. The primers for PCR amplification as shown below were synthesized (by Invitrogen Biological Technology Co. Ltd.):

```
Primer 1:
                                          SEQ ID NO: 7
5'-TAACCATGGGCCATCATCATCATCATCACGCCAACGCGTTCCTGGAG
      Nco I
GA-3'

Primer 2:
                                          SEQ ID NO: 8
5'-TATCTCGAGTTATCGGCCTTGGGGTTTGCTGGCATT-3'
      Xho I
```

2. PCR Amplification System

Figure 1:
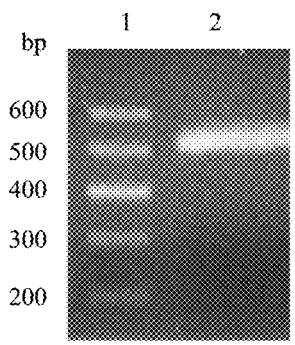
FIG. 1 is the electrophoregram of PCR amplification of the gene sequence encoding the recombinant protein LhF VII set forth in Example 1, wherein Lane 1 is the DNA molecular weight marker (Marker 1, purchased from TIANGEN BIOTECH Co. Ltd.) and Lane 2 is PCR amplification of the sequence encoding LhF VII.

The PCR amplification was performed with Primers 1 and 2 using a plasmid comprising the CDS region of human coagulation factor VII (FulenGen Co. Ltd., Guangzhou) as the template. An Nco I restriction site and a His×6 tag for protein purification were introduced into the sequence of Primer 1, and an Xho I restriction site was introduced into the sequence of Primer 2. After the amplification, a DNA fragment of 497 bp comprising the coding sequence for the human coagulation factor VII light chain was obtained. The PCR reaction system (50 µL) was as follows:
Deionized water: 31.5 µL
5×Reaction buffer: 10 µL
dNTP Mix: 4 µL
Primer 1 (10 mM): 1 µL
Primer 2 (10 mM): 1 µL
Plasmid comprising the CDS region of human coagulation factor VII (100 ng/µL): 2 µL
PrimeStar DNA polymerase: 0.5 µL 3. Reaction Conditions for the PCR Amplification The reaction condition for the PCR amplification was set with reference to the instruction of PrimeStar DNA polymerase (purchased from Takara): pre-denaturation at 98° C. for 2 min, 30 cycles of denaturation at 98° C. for 10 sec, annealing at 55° C. for 15 sec, and 72° C. elongation 50 sec, followed by elongation at 72° C. for 4 min 4. The amplified products were analyzed with 2% agarose gel electrophoresis (see FIG. 1) and the fragments of interest were recovered according to the instruction of a gel recovery kit (purchased from Omega).

Example 2

Obtaining the Gene Encoding the Recombination Protein LhF IX

1. The primers for PCR amplification as shown below were synthesized (by Invitrogen Biological Technology Co. Ltd.):

```
Primer 1:
                                          SEQ ID NO: 9
5'-ATACCATGGGCCATCATCATCATCATCATTATAATTCAGGTAAATT
      Nco I
GGAAG-3'

Primer 2:
                                          SEQ ID NO: 10
5'-ATTCTCGAGTTAACGGGTGAGCTTAGAAGTTTGT-3'
      Xho I
```

2. PCR Amplification System

The PCR amplification was performed with Primers 1 and 2 using a plasmid comprising the CDS region of human coagulation factor IX (FulenGen Co. Ltd., Guangzhou) as the template. An Nco I restriction site and a His×6 tag for protein purification were introduced into the sequence of Primer 1, and an Xho I restriction site was introduced into the sequence of Primer 2. After the amplification, a DNA fragment of 476 bp comprising the coding sequence for human coagulation factor IX light chain was obtained. The PCR reaction system (50 µL) was as follows:
Deionized water: 31.5 µL
5×Reaction buffer: 10 µL
dNTP Mix: 4 µL
Primer 1 (10 mM): 1 µL
Primer 2 (10 mM): 1 µL
Plasmid comprising the CDS region of human coagulation factor IX (100 ng/µL): 2 µL
PrimeStar DNA polymerase: 0.5 µL 3. Reaction Conditions for the PCR Amplification The reaction condition for the PCR amplification was set with reference to the instruction of PrimeStar DNA polymerase: pre-denaturation at 98° C. for 2 min, 30 cycles of denaturation at 98° C. for 10 sec, annealing at 55° C. for 15 sec, and 72° C. elongation for 50 sec, followed by elongation at 72° C. for 4 min.

Figure 2:
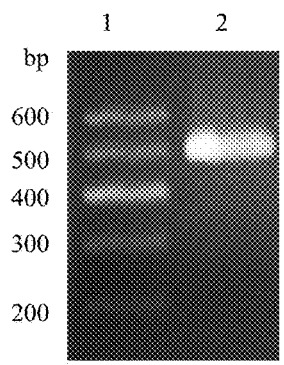
FIG. 2 is the electrophoregram of PCR amplification of the gene sequence encoding the recombinant protein LhF IX set forth in Example 2, wherein Lane 1 is the DNA molecular weight marker (Marker 1, purchased from TIANGEN BIOTECH Co. Ltd.) and Lane 2 is PCR amplification of the sequence encoding LhF IX.

4. The amplified products were analyzed with 2% agarose gel electrophoresis (see FIG. 2) and the fragments of interest were recovered according to the instruction of a gel recovery kit (purchased from Omega).

Example 3

Obtaining the Gene Encoding the Recombination Protein LhF X

1. The primers for PCR amplification as shown below were synthesized (by Invitrogen Biological Technology Co. Ltd.):

```
Primer 1:
                                  SEQ ID NO: 11
5'-ATACCATGGGCCATCATCATCATCATCATGCCAATTCCTTTCTTGA
      Nco I

AGAG-3'

Primer 2:
                                  SEQ ID NO: 12
5'-ATTCTCGAGTTAGCGTTCCAGGGTCTGTTTCC-3'
       Xho I
```

2. PCR Amplification System

The PCR amplification was performed with Primers 1 and 2 using a plasmid comprising the CDS region of human coagulation factor X (FulenGen Co. Ltd., Guangzhou) as the template. An Nco I restriction site and a His×6 tag for protein purification were introduced into the sequence of Primer 1, and an Xho I restriction site was introduced into the sequence of Primer 2. After the amplification, a DNA fragment of 458 bp comprising the coding sequence for the human coagulation factor X light chain was obtained. The PCR reaction system (50 μL) was as follows:

Deionized water: 31.5 μL
5×Reaction buffer: 10 μL
dNTP Mix: 4 μL
Primer 1 (10 mM): 1 μL
Primer 2 (10 mM): 1 μL
Plasmid comprising the CDS region of human coagulation factor X (100 ng/μL): 2 μL
PrimeStar DNA polymerase: 0.5 μL 3. Reaction Conditions for the PCR Amplification The reaction condition for the PCR amplification was set with reference to the instruction of PrimeStar DNA polymerase: pre-denaturation at 98° C. for 2 min, 30 cycles of denaturation at 98° C. for 10 sec, annealing at 55° C. for 15 sec, and 72° C. elongation for 50 sec, followed by elongation at 72° C. for 4 min.

Figure 3:
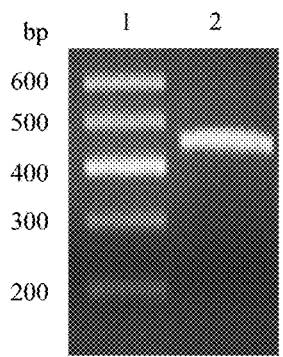
FIG. 3 is the electrophoregram of PCR amplification of the gene sequence encoding the recombinant protein LhF X set forth in Example 3, wherein Lane 1 is the DNA molecular weight marker (Marker 1, purchased from TIANGEN BIOTECH Co. Ltd.) and Lane 2 is PCR amplification of the sequence encoding LhF X.

4. The amplified products were analyzed with 2% agarose gel electrophoresis (see FIG. 3) and the fragments of interest were recovered according to the instruction of a gel recovery kit (purchased from Omega).

Example 4

Construction of the Recombinant Prokaryotic Plasmids for Expressing the Recombinant Proteins LhF VII, LhF IX, and LhF X 1. Pre-Treatment of the Gene Fragments and the Prokaryotic Expression Vector The LhF VII gene fragment cloned in Example 1, the LhF IX gene fragment cloned in Example 2, the LhF X gene fragment cloned in Example 3, and the prokaryotic expression vector pET19b (a product from Novagen) were individually double digested with the restriction endonucleases Nco I and Xho I (both purchased from TaKaRa or Fermentas), at 37° C. over night, and the reaction systems were set as follows:

| Reagent | LhF VII (μL) | LhF IX (μL) | LhF X (μL) | pET19b (μL) |
|---|---|---|---|---|
| DNA | 20 | 20 | 20 | 20 |
| Nco I | 1 | 1 | 1 | 1 |
| Xho I | 1 | 1 | 1 | 1 |
| 10 x Buffer | 6 | 6 | 6 | 6 |
| Double distilled water | 2 | 2 | 2 | 2 |
| Total volume | 30 | 30 | 30 | 30 |

After completion of the double digestion, the reaction products were analyzed with 1% agarose gel electrophoresis and the fragments of interest were recovered under the ultraviolet lamp of a gel imaging system according to the instruction of a gel recovery kit (purchased from Omega).

2. Ligation of LhF VII, LhF IX, and LhF X Genes to the Prokaryotic Expression Vector pET19b and Transformation (1) The gene fragments LhF VII, LhF IX, and LhF X and the prokaryotic vector fragment obtained in the above steps were quantified approximately and then subjected to ligation according to the ligation reaction principle where a ratio of the molecule number of the gene fragment to the molecule number of the prokaryotic vector is 3:1. The ligation reaction system was set up as follows:

| Reagent | Volume (μL) |
|---|---|
| pET19b DNA | 1.5 |
| LhF VII, LhF IX or LhF X DNA | 7 |
| T4 ligase | 0.5 |
| 10 x Buffer | 1 |
| Total volume | 10 |

Figure 4:
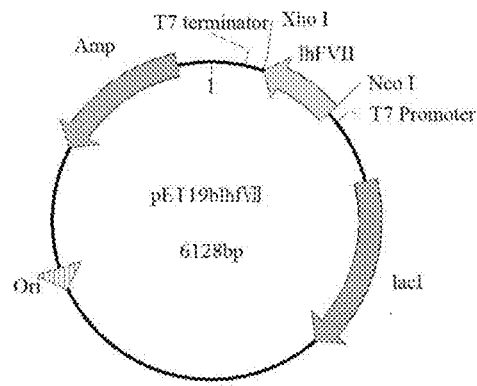
FIG. 4 is the schematic representation of the recombinant prokaryotic plasmid pET19blhf VII set forth in Example 4, wherein the counterclockwise sequence is the forward gene fragment and the clockwise one is the reverse gene fragment.
Figure 5:
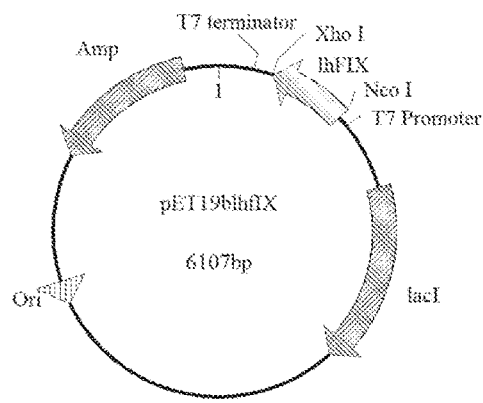
FIG. 5 is the schematic representation of the recombinant prokaryotic plasmid pET19blhf IX set forth in Example 4, wherein the counterclockwise sequence is the forward gene fragment and the clockwise one is the reverse gene fragment.
Figure 6:
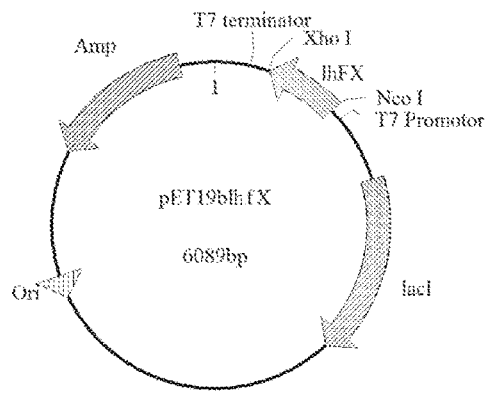
FIG. 6 is the schematic representation of the recombinant prokaryotic plasmid pET19blhf X set forth in Example 4, wherein the counterclockwise sequence is the forward gene fragment and the clockwise one is the reverse gene fragment.

(2) The entire ligation reaction was proceeded at 16° C. over night under the action of T4 DNA ligase (purchased from Fermentas). Each of the three gene fragments amplified above was inserted into the prokaryotic expression vector pET19b and the construction of the recombinant prokaryotic plasmids were schematically shown in FIGS. 4-6.

(3) Each of the ligation products was transformed into the competent cells (prepared according to Molecular Cloning: a Laboratory Manual) of *E. coli* Top10 (purchased from Invitrogen company). The main steps of the procedure for transforming the ligation products were as follows:

1) 5 μL of the ligation product was pipetted into 100 μl of the competent cells of *E. coli* Top10 placed in a 1.5 mL Eppendorf tube, and the negative control is 100 μl of the competent cells of *E. coli* Top10 placed in a 1.5 mL Eppendorf tube;

2) the tubes were placed on ice for 30 min;

3) the competent cells were shocked in a metal bath at 42° C. for 90 s;

4) the tubes were transferred rapidly into a ice-bath to be cooled for 2 min;

5) 900 μL of SOC medium (10 g peptone, 5 g yeast extract, 0.5 g NaCl, 0.186 g KCl, 0.95 g $MgCl_2$, dissolved with $ddH_2O$ and made up to a volume of 980 mL, autoclaved, cooled to room temperature and then 20 mL of sterile 20% aqueous glucose solution was added) was added, and placed on ice;

6) the tubes were incubated at 37° C. for 1 h with shaking at 180 rpm;

7) the bacterial suspension was centrifuged at 4000×g for 3 min, and the excessive medium was removed except 200

µL supernatant was kept. 200 µL of the remaining supernatant was used to resuspend the bacteria;

8) the resuspended transformants were plated uniformly onto the solid LB medium containing 0.1 g/mL ampicillin and incubated in a constant-temperature incubator at 37° C. over night.

3. Identification of the Recombinant Plasmid

The single clone of transformed *E. coli* Top 10 mentioned above was picked, cultured in a small quantity and subjected to plasmid extraction with a plasmid extraction kit (purchased from OMEGA), followed by double digestion with Nco I/Xho I for identification. The double digested product was identified by gel-electrophoresis. The electrophoregrams for identification of the restriction-endonuclease digested fragments of three recombinant plasmids are shown in FIGS. 7-9. The sizes of the two bands produced by the enzymatic digestion are consistent with those of the expected products, demonstrating the success of construction of the plasmid of interest.

The plasmids which had been identified by double digestion to be correct ones were send to Beijing Genomics Institute for sequencing of the inserted fusion gene fragments. Finally, the recombinant prokaryotic plasmid comprising the LhF VII gene with the correct sequencing result is designated as pET19blhf VII, the recombinant prokaryotic plasmid comprising the LhF IX gene as pET19blhf IX, and the recombinant prokaryotic plasmid comprising the LhF X gene as pET19blhf X.

Example 5

Expression of the Recombinant Prokaryotic Plasmid in *E. coli*

1. Each of the recombinant plasmids pET19blhf VII, pET19blhf IX, and pET19blhf X constructed in Example 4 was transformed into *E. coli* BL21 (DE3) (purchased from Invitrogen). The single clone was picked into the LB medium containing 0.1 g/mL of ampicillin and incubated at 37° C. to $OD_{600}$ of about 0.6 with shaking at 185 rpm. 1 mL of the bacterial suspension was taken and frozen at −20° C. Then, IPTG (isopropyl-p-D-thiogalactoside) was added to the remaining bacterial suspension at a final concentration of 0.8 mM. The incubation was proceeded for 6 h and 1 mL of the bacterial suspension was taken and frozen at −20° C.

2. The above-mentioned samples before and after IPTG induction were assayed by SDS-PAGE electrophoresis with 5% of the stacking gel and 12% of the separating gel, in order to analyze expression of the proteins of interest. The pictures of SDS-PAGE analysis on inducible expression of the recombinant proteins from the three recombinant plasmids in *E. coli* are seen in FIGS. 10-12, respectively. The results indicated that the proteins were expressed normally.

3. Western-blot identification of the proteins of interest. The proteins on the gel were electrotransfered onto a nitrocellulose filter membrane (GE). The electrotransfered membrane was blocked at room temperature with a blocking solution (PBST containing about 5% nonfat milk powder) in a shaking incubator for 2 h. Then, the dilutions of the mouse monoclonal antibodies directed against FVII, FIX, and FX (the products of Santa) were added respectively and incubated at 4° C. over night. After thorough washing, the enzymatically-labeled secondary antibody (goat anti-mouse IgG) was added and incubated at room temperature in a shaking incubator for 2 h. After thorough washing, the ECL (Thermo) reaction solution was added and incubated for 5 min, the blot was exposed to film and visualized. Western-blot images for analyzing and identifying the inducible expression of the three recombinant proteins are shown in FIGS. 13-15, respectively.

The results show that the fusion proteins are expressed obviously after IPTG induction. The strain expressing the LhF VII is designated as LhF VII-pET19bBL21-(DE3), the strain expressing the LhF IX as LhF IX-pET19bBL21-(DE3), and the strain expressing the LhF X as LhF X-pET19bBL21-(DE3).

Example 6

Purification of the Recombinant Proteins LhF VII, LhF IX, and LhF X by Affinity Chromatography 1. The bacteria LhF VII-pET19bBL21-(DE3), LhF IX-pET19bBL21-(DE3), and LhF X-pET19bBL21-(DE3) were cultured in large scale according to the method in Example 5, induced by addition of IPTG, and then cultured over night at 18° C., with shaking at 175 rpm.

2. The above-mentioned bacterial suspension was centrifuged at 4000×g for 3 min to collect the bacteria. The bacterial pellet was washed by resuspension in the EW buffer (20 mM sodium phosphate, 500 mM NaCl, 1 mM DTT, 0.1 mM PMSF, pH 7.4). The bacterial suspension was centrifuged at 4000×g for 3 min, and the supernatant was discarded. Again, the bacterial pellet was resuspended with 10 mL of the EW buffer.

3. The bacteria were disrupted by sonication (power: 300 W; duration for sonication: 10 s; interval: 10 s; total time for sonication: 3 min; performed in ice-bath). After completion of the sonication, the bacterial suspension was centrifuged at 48400×g at 4° C. for 30 min. The supernatant was collected and placed on ice.

4. The chromatographic column was preloaded according to the instruction of $Co^{2+}$ purification system (Talon Metal Affinity Resin, Clontech company product), and the sample was loaded. The column was washed twice with 10 mL EW buffer and the protein impurities were washed out with 10 mM imidazole solution. Finally, the protein was eluted with 100 mM imidazole. SDS-PAGE images for analyzing and identifying the three recombinant proteins purified by affinity chromatography are seen in FIGS. 16-18, respectively.

5. The eluent comprising the proteins of interest was ultrafiltrated with Tris-Cl buffer (pH 7.4) for buffer exchange and concentration. After ultrafiltration, the high concentrations of the recombinant proteins, i.e. LhF VII, LhF IX, and LhF X, can be obtained. Protein quantitation showed that 15 mg of the proteins of interest with more than 90% of purity can be obtained per liter of the expressing bacterium suspension.

Example 7

Construction of the Recombinant Eukaryotic Plasmids for Expressing the Recombinant Proteins LhF VII, LhF IX, and LhF X 1. The primers for PCR amplification as shown below were synthesized (by Invitrogen Biological Technology Co. Ltd.):

```
Primer 1:
                                       SEQ ID NO: 13
TAAGGATCCTGCAGAGATTTCATCATGGTCTCCCA
    BamH I   Kozak
```

-continued

```
Primer 2:
                                    SEQ ID NO: 14
TATCTCGAGTTAATGATGATGATGATGATGTCGGCCTTGG
    Xho I         6×His Primer 3:
                                    SEQ ID NO: 15
TAAGGATCCTGCAGAGATTTCATCATGCAGCGCGTGAAC
    BamH I    Kozak Primer 4:
                                    SEQ ID NO: 16
TATCTCGAGTTAATGATGATGATGATGATGACGGGTGAGCT
    Xho I         6×His Primer 5:
                                    SEQ ID NO: 17
TAAGGATCCTGCAGAGATTTCATCATGGGGCGCCCA
    BamH I    Kozak Primer 6:
                                    SEQ ID NO:18
TATCTCGAGTTAATGATGATGATGATGATGGCGTTCCA
    Xho I         6×His
```

2. PCR Amplification System

The PCR amplification was performed with Primers 1 and 2 using a plasmid comprising the CDS region of human coagulation factor VII (FulenGen Co. Ltd., Guangzhou) as the template. A BamH I restriction site and a Kozak sequence were introduced into the sequence of Primer 1, and an Xho I restriction site and a His×6 tag for protein purification were introduced into the sequence of Primer 2. The PCR amplification was performed with Primers 3 and 4 using a plasmid comprising the CDS region of human coagulation factor IX (FulenGen Co. Ltd., Guangzhou) as the template. A BamH I restriction site, a Kozak sequence and a signal peptide sequence were introduced into the sequence of Primer 3, and an Xho I restriction site and a His×6 tag for protein purification were introduced into the sequence of Primer 4. The PCR amplification was performed with Primers 5 and 6 using a plasmid comprising the CDS region of human coagulation factor X (FulenGen Co. Ltd., Guangzhou) as the template. A BamH I restriction site, a Kozak sequence and a signal peptide sequence were introduced into the sequence of Primer 5, and an Xho I restriction site and a His×6 tag for protein purification were introduced into the sequence of Primer 6.

The PCR reaction was performed with reference to Example 1.

3. Construction of the Recombinant Plasmids for Eukaryotic Expression of the Recombinant Proteins LhF VII, LhF IX, and LhF X The gene fragments LhF VII, LhF IX, and LhF X cloned in Example 7 and the eukaryotic expression vector pcDNA3.1 (+) (the product from Novagen) were individually double digested with the restriction endonucleases BamH I and Xho I (both purchased from TaKaRa Fermentas), and the reaction systems were set up with reference to Example 4. The steps for ligating the genes to the eukaryotic expression vector and for transforming and identifying the recombinant plasmids were referred to Example 4.

Finally, the recombinant plasmid comprising the LhF VII gene with the correct sequencing result is designated as pcDNA3.1-LhF VII, the recombinant plasmid comprising the LhF IX gene as pcDNA3.1-LhF IX, and the recombinant plasmid comprising the LhF X gene as pcDNA3.1-LhF X. The plasmid maps can be seen in FIGS. 19-21.

Example 8

Construction of Stable Cell Lines for Expressing the Recombinant Proteins LhF VII, LhF IX, and LhF X 1. Cell Preparation DG44 cells (purchased from ATCC) were cultured in the α-MEM (containing L-glutamine, ribonucleic acid and deoxyribonucleic acid) complete culture medium (purchased from Hiclony) supplemented with 10% FBS (fetal bovine serum, purchased from Hiclony). On the day before transfection, DG44 cells were seeded in a 6-well plate at $4 \times 10^5$ cells/mL with 2 mL per well.

2 Cell Transfection

Cells were transfected with liposomes, following the instruction of Lipofectamine™2000 kit (purchased from Invitrogen). The detailed steps are as follows:

1) The cell culture medium was replaced with a serum-free α-MEM medium, 2 mL/well.

2) The eukaryotic recombinant plasmids pcDNA3.1-LhF VII, pcDNA3.1-LhF IX, and pcDNA3.1-LhF X (total amount of 4.0 μg) were individually mixed with 250 μL Opti-MEM, while 10 μl of lipo2000 was mixed with 250 μL of Opti-MEM and incubated for 5 min 3) The two solutions were mixed well and incubated for 20 min. The liposome complex was added into the well with cells, gently mixed, placed into an incubator and cultured at 37° C.

4) After 5 h, the medium was replaced with the α-MEM complete culture medium supplemented with 10% FBS;

3. Screening and Expanding of the Positive Cell Clones

After 24 h of transfection with the recombinant plasmids, the cells were transferred into 100 mm petri dishes at a ratio of 1:2000. G418 (purchased from Gibco) was added at a final concentration of 800 μg/mL for screening. Cells transfected with an empty vector or not transfected were used as controls. After 15 days, the single clones were picked into and cultured in 24-well plates, and sequentially transferred into 6-well plates and into 100 mm petri dishes for expanding culture once cellular confluence was reached. When the cell confluency was 90%, cells were frozen at a rate of 1:4 in FBS with 10% DMSO (purchased from Gibco).

4. Identification of the Positive Cell Clones

The picked positive cell clones were identified by the genomic PCR and RT-PCR. The fragments of interest could be amplified by both of the techniques, which demonstrated that the fusion gene has been integrated into the genome of the cell and a functional mRNA is transcribed. The stable cell lines obtained were designated as DG44-LhF VII, DG44-LhF IX, and DG44-LhF X, respectively.

Example 9

Collection of the Recombinant Proteins LhF VII, LhF IX, and LhF X Expressed by the Recombinant Eukaryotic Plasmids 1. The cells DG44-LhF VII, DG44-LhF IX, DG44-LhF X were cultured respectively in the α-MEM complete culture medium containing 10% FBS supplemented with 400 μg/mL G418, and passaged into 10 plates.

2. When the cell confluency in each plate reached more than 90%, the α-MEM complete culture medium containing 10% FBS was replaced with CHO serum-free medium, and supplemented with Vitamin K (Sigma) to a final concentration of 1 μg/mL.

3. After 3 days of cultivation, the culture supernatant was collected and centrifuged. The cellular pellet was discarded. The supernatant was five-fold concentrated with PEG20000 (Merck), purified by cobalt ion affinity chromatography and identified by SDS-PAGE and Western Blot. All steps were referred to those in Example 6.

Example 10

Detection of the Antibacterial Activity of the Recombinant Proteins LhF VII, LhF IX, and LhF X 1. *E. coli* DH5α was exemplified. *E. coli* DH5α was streaked and cultured on LB solid medium. Then, a typical clone was picked and inoculated into common LB liquid medium, cultured at 37° C. with shaking at 185 rpm until the logarithmic growth phase was reached ($OD_{600}$ of about 0.5). The bacterial culture was centrifuged at 4000×g for 3 min, the supernatant was discarded, and the thalli were resuspended with fresh LB medium.
2. The above-mentioned bacterial suspension was diluted and inoculated into a 96-well plate with the total volume of 100 μL per well and a bacterial count of $5 \times 10^5$ CFU/mL.
3. The recombinant proteins LhF VII, LhF IX, and LhF X were added individually to the above-mentioned wells with the final protein concentration in the well of the highest protein concentration being 50 μg/mL. Basing on this final concentration, a two-fold serial dilution was performed till a protein concentration gradient consisting of 50, 25, and 12.5 μg/mL was set up. Three parallel wells were set up for each concentration in the gradient. Meanwhile, a blank well with no bacteria and a protein-free well with bacteria alone were set up, three parallel wells per group.
4. The above-mentioned 96-well plate was placed and cultured at 37° C. in a shaking incubator shaking at 175 rpm. Samples were taken every 30 min, the absorbance values were determined at 600 nm wavelength under an ultra violet spectrophotometer, and an inhibition curve was plotted. Judgement on MIC: After 8 h of cultivation, the growth was observed with naked eyes or judged under the ultra violet spectrophotometer at a wavelength of 600 nm. The minimal inhibitory concentration MIC is defined as the lowest concentration of the recombinant protein at which there is no growth of the bacteria.

The growth curves of *E. coli* DH5α treated with the recombinant proteins LhF VII, LhF IX, and LhF X are seen in FIGS. 22-24. It can be known from the FIGS. 22-24 that the recombinant proteins LhF VII, LhF IX, and LhF X have a significant inhibitory effect on the growth of DH5α and that the MICs for the recombinant proteins LhF VII, LhF IX, and LhF X respectively were 25 μg/mL.

5. The effects of the recombinant proteins LhF VII, LhF IX, and LhF X on the growth of the Gram negative bacteria such as *E. coli* BL21, *Pseudomonas aeruginosa*, *Klebsiella pneumonia*, *Enterobacter cloacae*, *Aeromonas hydrophila*, *Citrobacter diversus*, *Moraxella catarrhalis*, *Proteus mirabilis*, *Proteus vulgaris*, *Serratia marcescens* were tested with the same method as that for *E. coli* DH5α. The MICs for these bacteria were listed in the table below:

| Strain | MIC (μg/mL) | | |
|---|---|---|---|
| | LhF VII | LhF IX | LhF X |
| *E. coli* BL21 | 50 | 50 | 50 |
| *P. aeruginosa* | 25 | 25 | 25 |
| *K. pneumonia* | 25 | 25 | 25 |
| *E. cloacae* | 25 | 50 | 50 |
| *A. hydrophila* | 25 | 25 | 25 |
| *C. diversus* | 50 | 50 | 25 |
| *M. catarrhalis* | 25 | 25 | 25 |
| *P. mirabilis* | 25 | 25 | 25 |
| *P. vulgaris* | 50 | 50 | 25 |
| *S. marcescens* | 25 | 50 | 25 |

Conclusion: It can be known from the above-mentioned experimental results that the recombinant proteins LhF VII, LhF IX, and LhF X set forth in the present invention all have significant inhibitory effect on various Gram-negative bacteria.

Example 11

Determination of the Antibacterial Activity of the Recombinant Proteins LhF VII, LhF IX, and LhF X in Animals 1. The laboratory animal are male BAL B/C mice (body weight of about 18-22 g, from Sichuan University) and assigned into 11 groups with 8 animals/group, of which 3 groups are the experimental groups and the remainder are the various control groups.
2. The bacterial suspension of *P. aeruginosa* (derived from Sichuan University) was streaked and cultured on LB solid medium. Then, a typical clone was picked and inoculated into common LB liquid medium, cultured at 37° C. over night for about 12 h with shaking, and subsequently centrifuged at 4000×g for 3 min. The supernatant was discarded and the bacterial pellet was resuspended with physiological saline for the future use.
3. According to aseptic manipulation, the recombinant proteins LhF VII, LhF IX, and LhF X were individually formulated with physiological saline into a sample at a concentration of 100 μg/mL, and hold on ice for the future use.
4. Penicillin and meropenem were dissolved individually with sterile physiological saline and converted into the clinically equivalent dose in a male BAL B/C mouse on the basis of the body surface area of an adult of 60 kg. The clinically equivalent dose for penicillin is 9.1 mg/animal, and for meropenem 1.5 mg/animal.
5. The bacterial suspension comprising the lethal dose of *P. aeruginosa* was injected intraperitoneally into the male BAL B/C mice in the individual experimental groups and the three control groups at a dosage of 500 μL/animal.
6. After the male BAL B/C mice in the three experimental groups were infected with the bacteria for 30 min, the mice in the first experimental group was dosed with the recombinant protein LhF VII (50 μg/animal) via the tail, the mice in the second experimental group with the recombinant protein LhF IX (100 μg/animal) via the tail, the mice in the third experimental group with the recombinant protein LhF X (100 μg/animal) via the tail. After the male BAL B/C mice in the three control groups were infected with the bacteria for 30 min, the mice in the first and second control groups were dosed respectively with penicillin (9.1 mg/animal) and meropenem (1.5 mg/animal) via the tail, and the mice in the third control group were not dosed. The mice in the remaining control groups, i.e., the fourth, fifth, sixth, seventh, eighth control groups, were not injected with the bacterial suspension of *P. aeruginosa*, but were injected respectively with the same doses of the recombinant proteins LhF VII, LhF IX, and LhF X as those in the first, second, and third experimental groups, and respectively with the same doses of penicillin and meropenem as those in the first and second control groups.

7. At 72 h post-dosing, the male BAL B/C mice in the individual experimental groups and the individual control groups were dosed secondly with the same types and doses of the medicaments as those in the first administration.

8. After the dosing, the male BAL B/C mice were observed once every 24 h and the survival condition of the mice was documented. On the 15$^{th}$ day, all animals were sacrificed.

The survival rate=the surviving mice/8×100%

The experimental results: The recombinant proteins LhF VII, LhF IX, and LhF X set forth in the present invention can keep the 100% of mice infected with the lethal dose of *P. aeruginosa* surviving for 14 days. The survival rate in the mice in the second control group (the meropenem group) was 100% after 14 days, however, all of the mice in the first control group (the penicillin group) died. The survival rates of the mice infected with the lethal dose of *P. aeruginosa* are shown in FIGS. 25-27. All of the mice in the fourth, fifth, sixth, seventh, and eighth control groups survived.

The experimental results show that the recombinant proteins LhF VII, LhF IX, and LhF X set forth in the present invention have an inhibitory effect on the Gram-negative bacteria in the animals, also have low toxicity, and do not result in the death of the animals.

Example 12

Mass Spectrometric Detection of Destruction of the Endotoxin (LPS) by the Recombination Proteins LhF VII, LhF IX, and LhF X 1. 1 mg/mL of *E. coli* K12 LPS (Sigma) was treated with the recombination protein LhF VII, LhF IX, or LhF X obtained in Example 6. The systems were set up as follows:

| | | |
|---|---|---|
| The experimental group: | 0.5 µg/µL LhF VII, LhF IX, or LhF X | 120 µL |
| | 1 mg/mL LPS | 250 µL |
| | Physiological saline | 30 µL |
| The control group 1: | 0.5 µg/µL LhF VII, LhF IX, or LhF X | 120 µL |
| | Physiological saline | 280 µL |
| The control group 2: | TBS | 120 µL |
| | 1 mg/mL LPS | 250 µL |
| | Physiological saline | 30 µL |

2. The systems mentioned above were incubated overnight at 37° C. at 150 rpm. After completion of the incubation, samples were centrifuged at the maximal rotation speed of 17000 g for 5 min. The supernatants were collected after completion of centrifugation.

3. The supernatants were dialyzed for 16 h in a 100 D dialysis bag against dialysis buffer which was deionized water. After completion of the dialysis, the treated samples were analyzed by MALDI-TOF.

4. Firstly, 1 µL of 10 mg/mL 2,5-dihydroxybenzoic acid (DHB) dissolved in 33% alcohol was mixed well with 1 µL of the sample.

5 The sample mixed with DHB was dropped onto the stainless-steel target plate MTP 384 (Bruker Daltonics), followed by drying the sample completely on the target plate with hot air.

6. After drying, the analysis was performed using Autoflex TOF/TOF II apparatus (Bruker) with a nitrogen laser beam at 377 nm under positive ion mode. Operations were controlled by the software FlexControl 2.2. The whole mass spectra were acquired in the reflector mode at an accelerating voltage of 90 kV and a reflector voltage of 20 kV. Pulses were excited under positive ion mode for 140 ns. The scanning range is within the mass-to-charge ratio of 600 to 7000. The time of period for data collection was 500 laser pulses on average, of which the minimal laser energy must be capable of achieving the sufficient signal-to-noise ratio. The peaks generated in the mass spectrometry were acquired by using Bruker Flex analysis software (Version 3.0).

7. The post-source decay (PSD) mass spectra were recorded with the Bruker Daltonics LIFT system at a precursor-ion accelerating voltage of 18.96 kV and a fragment acceleration voltage of 4.37 kV (LIFT). The reflector voltages 1 and 2 were set at 23.49 kV and 9.69 kV, respectively.

The spectrum of the experiment was exemplified by LhF VII and the result is shown in FIG. 28. There is an obvious peak of m/z 2318.4 from the untreated LPS (middle) and the peak of m/z 2318.4 is absent in the peaks in the mass spectrum after treatment of LPS with LhF VII (bottom), indicating hydrolysis of LPS by the light-chain protein. Accordingly, LhF VII, LhF IX, and LhF X set forth in the present invention can hydrolyze LPS and be useful in treatment of endotoxemia Example 13

Silver Staining Detection of the *E. coli* K12 LPS Hydrolyzed by the Recombination Proteins LhF VII, LhF IX, and LhF X 1. The LPS samples were respectively incubated with the recombinant proteins LhF VII, LhF IX, and LhF X obtained in Example 6 and the control group was the LPS sample incubated with TBS buffer. The incubation lasted overnight. Then, the centrifugation was performed to collect the pellet.

2. The 1×loading buffer for LPS (0.05 M Tris-HCl, containing 10 g/L SDS, 100 g/L sucrose, 0.5% β-mercaptoethanol, 10 mg/L Bromophenol Blue, pH 6.8) was mixed with the sample of the treated pellet and incubated on a metal bath at 100° C. for 5 min.

3. 15% of the separating gel (containing 4 mol/L urea, Bio-Rad with a thickness of 1.0 mm, the detailed composition as follows: 1.15 mL of deionized water, 2.5 mL of 30% acrylamide, 1.3 mL of 1.5 mol/L Tris-HCl (pH 8.8, containing 10% SDS), 50 µL of 10% ammonium persulfate, 4 µL of TEMED) was mixed well and prepared. The top of the separating gel was overlaid with water.

4. 5% stacking gel was prepared as follows: 1.42 mL of deionized water, 0.33 mL of 30% acrylamide, 0.25 mL of 1 mol/L Tris-HCl (pH 6.8, containing 10% SDS), 20 µL of 10% ammonium persulfate, 2 µl of TEMED) were mixed well and poured. A ten-well comb was quickly inserted.

5. After the gel was prepared, the samples were loaded. Then, the gel was run at a voltage of 120 V to separate the samples. After running, gel was taken to start silver staining. The gel was transferred into a tray washed thoroughly with deionized water, followed by washing the gel three times with deionized water.

6. After completion of the washing, the gel was fixed with 50 mL of fixation solution (30% alcohol, 10% glacial acetic acid, 7 g/L periodic acid) for oxidation at room temperature for 25 min After completion of the fixation, the gel was washed three times each time with deionized water for 5 min.

7. After completion of the washing, the gel was stained in 100 mL of 1 g/L AgNO$_3$ at room temperature for 40 min After completion of the staining, the gel was washed one time with ddH$_2$O.

8. The gel was transferred into 50 mL of 30 g/L Na$_2$CO$_3$ pre-chilled on ice, to which 0.02% of formaldehyde was added just before visualization. When the band appeared or began to become dark, the reaction was stopped by adding 6 mL of glacial acetic acid. The stopping solution was removed upon completion of the termination reaction and the gel was kept in deionized water.

The silver staining picture was exemplified by LhF VII, as shown in FIG. 29. After treated with LhF VII, the LPS band is obviously decreased and becomes weak, indicating that the light chain-protein eliminates the majority of LPS. Accordingly, LhF VII, LhF IX, and LhF X set forth in the present invention can hydrolyze LPS and be useful in treatment of endotoxemia.

The invention claimed is:

1. A method for treating a disease caused by Gram-negative bacteria infection, said method comprises administering an effective amount of protein encoded by a human coagulation factor light-chain gene or a pharmaceutical composition thereof to a subject.

2. The method of claim 1, wherein the disease caused by Gram-negative bacteria infection is endotoxemia.

3. The method of claim 1, wherein the protein encoded by a human coagulation factor light-chain gene comprises amino acid sequence SEQ ID NO:1, SEQ ID NO:2, SEQ ID NO:3 or combinations thereof.

4. The method of claim 2, wherein the protein encoded by a human coagulation factor light-chain gene comprises amino acid sequence SEQ ID NO:1, SEQ ID NO:2, SEQ ID NO:3 or any combination thereof.

5. The method of claim 1, wherein the Gram-negative bacteria is one or more of *Escherichia coli, Pseudomonas aeruginosa, Klebsiella pneumonia, Enterobacter cloacae, Aeromonas hydrophila, Citrobacter diversus, Moraxella catarrhalis, Proteus mirabilis, Proteus vulgaris* and *Serratia marcescens*.

6. The method of claim 2, wherein the Gram-negative bacteria is one or more of *Escherichia coli, Pseudomonas aeruginosa, Klebsiella pneumonia, Enterobacter cloacae, Aeromonas hydrophila, Citrobacter diversus, Moraxella catarrhalis, Proteus mirabilis, Proteus vulgaris* and *Serratia marcescens*.

7. The method of claim 3, wherein the Gram-negative bacteria is one or more of *Escherichia coli, Pseudomonas aeruginosa, Klebsiella pneumonia, Enterobacter cloacae, Aeromonas hydrophila, Citrobacter diversus, Moraxella catarrhalis, Proteus mirabilis, Proteus vulgaris* and *Serratia marcescens*.

8. The method of claim 4, wherein the Gram-negative bacteria is one or more of *Escherichia coli, Pseudomonas aeruginosa, Klebsiella pneumonia, Enterobacter cloacae, Aeromonas hydrophila, Citrobacter diversus, Moraxella catarrhalis, Proteus mirabilis, Proteus vulgaris* and *Serratia marcescens*.

9. A method for hydrolyzing a lipopolysaccharide, said method comprising contacting a lipopolysaccharide with an effective amount of protein encoded by a human coagulation factor light-chain gene or a pharmaceutical composition thereof to hydrolyze the lipopolysaccharide.

10. The method of claim 9, wherein the lipopolysaccharide is a lipopolysaccharide of a Gram-negative bacteria.

11. The method of claim 10, wherein the Gram-negative bacteria is one or more of *Escherichia coli, Pseudomonas aeruginosa, Klebsiella pneumonia, Enterobacter cloacae, Aeromonas hydrophila, Citrobacter diversus, Moraxella catarrhalis, Proteus mirabilis, Proteus vulgaris* and *Serratia marcescens*.

12. The method of claim 9, wherein the protein encoded by a human coagulation factor light-chain gene comprises amino acid sequence SEQ ID NO:1, SEQ ID NO:2, SEQ ID NO:3 or any combination thereof.

13. The method of claim 10, wherein the protein encoded by a human coagulation factor light-chain gene comprises amino acid sequence SEQ ID NO:1, SEQ ID NO:2, SEQ ID NO:3 or any combination thereof.

14. The method of claim 11, wherein the protein encoded by a human coagulation factor light-chain gene comprises amino acid sequence SEQ ID NO:1, SEQ ID NO:2, SEQ ID NO:3 or any combination thereof.

* * * * *

SEQUENCE LISTING

```
<160> NUMBER OF SEQ ID NOS: 18

<210> SEQ ID NO 1
<211> LENGTH: 152
<212> TYPE: PRT
<213> ORGANISM: Homo sapiens
<220> FEATURE:
<221> NAME/KEY: MISC_FEATURE
<222> LOCATION: (1)..(152)
<223> OTHER INFORMATION: Light chain protein of human coagulation factor
      VII

<400> SEQUENCE: 1

Ala Asn Ala Phe Leu Glu Glu Leu Arg Pro Gly Ser Leu Glu Arg Glu
1               5                   10                  15

Cys Lys Glu Glu Gln Cys Ser Phe Glu Glu Ala Arg Glu Ile Phe Lys
            20                  25                  30

Asp Ala Glu Arg Thr Lys Leu Phe Trp Ile Ser Tyr Ser Asp Gly Asp
        35                  40                  45

Gln Cys Ala Ser Ser Pro Cys Gln Asn Gly Gly Ser Cys Lys Asp Gln
    50                  55                  60

Leu Gln Ser Tyr Ile Cys Phe Cys Leu Pro Ala Phe Glu Gly Arg Asn
65                  70                  75                  80

Cys Glu Thr His Lys Asp Asp Gln Leu Ile Cys Val Asn Glu Asn Gly
                85                  90                  95

Gly Cys Glu Gln Tyr Cys Ser Asp His Thr Gly Thr Lys Arg Ser Cys
            100                 105                 110

Arg Cys His Glu Gly Tyr Ser Leu Leu Ala Asp Gly Val Ser Cys Thr
        115                 120                 125

Pro Thr Val Glu Tyr Pro Cys Gly Lys Ile Pro Ile Leu Glu Lys Arg
    130                 135                 140

Asn Ala Ser Lys Pro Gln Gly Arg
145                 150

<210> SEQ ID NO 2
<211> LENGTH: 145
<212> TYPE: PRT
<213> ORGANISM: Homo sapiens
<220> FEATURE:
<221> NAME/KEY: MISC_FEATURE
<222> LOCATION: (1)..(145)
<223> OTHER INFORMATION: Light chain protein of human coagulation factor
      IX

<400> SEQUENCE: 2

Tyr Asn Ser Gly Lys Leu Glu Glu Phe Val Gln Gly Asn Leu Glu Arg
1               5                   10                  15

Glu Cys Met Glu Glu Lys Cys Ser Phe Glu Glu Ala Arg Glu Val Phe
            20                  25                  30
```

```
Glu Asn Thr Glu Arg Thr Thr Glu Phe Trp Lys Gln Tyr Val Asp Gly
         35                  40                  45

Asp Gln Cys Glu Ser Asn Pro Cys Leu Asn Gly Gly Ser Cys Lys Asp
 50                  55                  60

Asp Ile Asn Ser Tyr Glu Cys Trp Cys Pro Phe Gly Phe Glu Gly Lys
 65                  70                  75                  80

Asn Cys Glu Leu Asp Val Thr Cys Asn Ile Lys Asn Gly Arg Cys Glu
             85                  90                  95

Gln Phe Cys Lys Asn Ser Ala Asp Asn Lys Val Val Cys Ser Cys Thr
            100                 105                 110

Glu Gly Tyr Arg Leu Ala Glu Asn Gln Lys Ser Cys Glu Pro Ala Val
        115                 120                 125

Pro Phe Pro Cys Gly Arg Val Ser Val Ser Gln Thr Ser Lys Leu Thr
    130                 135                 140

Arg
145

<210> SEQ ID NO 3
<211> LENGTH: 139
<212> TYPE: PRT
<213> ORGANISM: Homo sapiens
<220> FEATURE:
<221> NAME/KEY: MISC_FEATURE
<222> LOCATION: (1)..(139)
<223> OTHER INFORMATION: Light chain protein of human coagulation factor
      X

<400> SEQUENCE: 3

Ala Asn Ser Phe Leu Glu Glu Met Lys Lys Gly His Leu Glu Arg Glu
1               5                  10                  15

Cys Met Glu Glu Thr Cys Ser Tyr Glu Glu Ala Arg Glu Val Phe Glu
            20                  25                  30

Asp Ser Asp Lys Thr Asn Glu Phe Trp Asn Lys Tyr Lys Asp Gly Asp
         35                  40                  45

Gln Cys Glu Thr Ser Pro Cys Gln Asn Gln Gly Lys Cys Lys Asp Gly
 50                  55                  60

Leu Gly Glu Tyr Thr Cys Thr Cys Leu Glu Gly Phe Glu Gly Lys Asn
65                  70                  75                  80

Cys Glu Leu Phe Thr Arg Lys Leu Cys Ser Leu Asp Asn Gly Asp Cys
             85                  90                  95

Asp Gln Phe Cys His Glu Glu Gln Asn Ser Val Val Cys Ser Cys Ala
            100                 105                 110

Arg Gly Tyr Thr Leu Ala Asp Asn Gly Lys Ala Cys Ile Pro Thr Gly
        115                 120                 125

Pro Tyr Pro Cys Gly Lys Gln Thr Leu Glu Arg
    130                 135

<210> SEQ ID NO 4
<211> LENGTH: 459
<212> TYPE: DNA
<213> ORGANISM: Homo sapiens
<220> FEATURE:
<221> NAME/KEY: misc_feature
<222> LOCATION: (1)..(459)
<223> OTHER INFORMATION: Polynucleotide sequence for light chain of
      human coagulation factor VII

<400> SEQUENCE: 4
gccaacgcgt tcctggagga gctgcggccg ggctccctgg agagggagtg caaggaggag    60
```

```
cagtgctcct tcgaggaggc ccgggagatc ttcaaggacg cggagaggac gaagctgttc    120
tggatttctt acagtgatgg ggaccagtgt gcctcaagtc catgccagaa tgggggctcc    180
tgcaaggacc agctccagtc ctatatctgc ttctgcctcc ctgccttcga gggccggaac    240
tgtgagacgc acaaggatga ccagctgatc tgtgtgaacg agaacggcgg ctgtgagcag    300
tactgcagtg accacacggg caccaagcgc tcctgtcggt gccacgaggg gtactctctg    360
ctggcagacg gggtgtcctg cacacccaca gttgaatatc catgtggaaa aatacctatt    420
ctagaaaaaa gaaatgccag caaaccccaa ggccgataa                           459
```

<210> SEQ ID NO 5
<211> LENGTH: 438
<212> TYPE: DNA
<213> ORGANISM: Homo sapiens
<220> FEATURE:
<221> NAME/KEY: misc_feature
<222> LOCATION: (1)..(438)
<223> OTHER INFORMATION: Polynucleotide sequence for light chain of
      human coagulation factor IX

<400> SEQUENCE: 5

```
tataattcag gtaaattgga agagtttgtt caagggaacc ttgagagaga atgtatggaa     60
gaaaagtgta gttttgaaga agcacgagaa gttttgaaa acactgaaag aacaactgaa     120
ttttggaagc agtatgttga tggagatcag tgtgagtcca atccatgttt aaatggcggc    180
agttgcaagg atgacattaa ttcctatgaa tgttggtgtc cctttggatt tgaaggaaag    240
aactgtgaat tagatgtaac atgtaacatt aagaatggca gatgcgagca gttttgtaaa    300
aatagtgctg ataacaaggt ggtttgctcc tgtactgagg gatatcgact tgcagaaaac    360
cagaagtcct gtgaaccagc agtgccattt ccatgtggaa gagtttctgt ttcacaaact    420
tctaagctca cccgttaa                                                  438
```

<210> SEQ ID NO 6
<211> LENGTH: 420
<212> TYPE: DNA
<213> ORGANISM: Homo sapiens
<220> FEATURE:
<221> NAME/KEY: misc_feature
<222> LOCATION: (1)..(420)
<223> OTHER INFORMATION: Polynucleotide sequence for light chain of
      human coagulation factor X

<400> SEQUENCE: 6

```
gccaattcct tcttgaaga gatgaagaaa ggacacctcg aaagagagtg catggaagag     60
acctgctcat acgaagaggc ccgcgaggtc tttgaggaca gcgacaagac gaatgaattc    120
tggaataaat acaaagatgg cgaccagtgt gagaccagtc cttgccagaa ccagggcaaa    180
tgtaaagacg gcctcgggga atacacctgc acctgtttag aaggattcga aggcaaaaac    240
tgtgaattat tcacacggaa gctctgcagc ctggacaacg gggactgtga ccagttctgc    300
cacgaggaac agaactctgt ggtgtgctcc tgcgcccgcg gtacaccct ggctgacaac    360 ggcaaggcct gcattcccac agggccctac ccctgtggga acagaccct ggaacgctaa    420
```

<210> SEQ ID NO 7
<211> LENGTH: 49
<212> TYPE: DNA
<213> ORGANISM: Artificial Sequence
<220> FEATURE:
<223> OTHER INFORMATION: primer 1 for recombination protein LhFVII

<400> SEQUENCE: 7
taaccatggg ccatcatcat catcatcacg ccaacgcgtt cctggagga          49

<210> SEQ ID NO 8
<211> LENGTH: 36
<212> TYPE: DNA
<213> ORGANISM: Artificial Sequence
<220> FEATURE:
<223> OTHER INFORMATION: primer 2 for recombination protein LhFVII

<400> SEQUENCE: 8
tatctcgagt tatcggcctt ggggtttgct ggcatt                        36

<210> SEQ ID NO 9
<211> LENGTH: 51
<212> TYPE: DNA
<213> ORGANISM: Artificial Sequence
<220> FEATURE:
<223> OTHER INFORMATION: primer 1 for recombination protein LhFIX

<400> SEQUENCE: 9
ataccatggg ccatcatcat catcatcatt ataattcagg taaattggaa g       51

<210> SEQ ID NO 10
<211> LENGTH: 34
<212> TYPE: DNA
<213> ORGANISM: Artificial Sequence
<220> FEATURE:
<223> OTHER INFORMATION: primer 2 for recombination protein LhFIX

<400> SEQUENCE: 10
attctcgagt taacgggtga gcttagaagt ttgt                          34

<210> SEQ ID NO 11
<211> LENGTH: 50
<212> TYPE: DNA
<213> ORGANISM: Artificial Sequence
<220> FEATURE:
<223> OTHER INFORMATION: primer 1 for recombination protein LhFX

<400> SEQUENCE: 11
ataccatggg ccatcatcat catcatcatg ccaattcctt tcttgaagag         50

<210> SEQ ID NO 12
<211> LENGTH: 32
<212> TYPE: DNA
<213> ORGANISM: Artificial Sequence
<220> FEATURE:
<223> OTHER INFORMATION: primer 2 for recombination protein LhFX

<400> SEQUENCE: 12
attctcgagt tagcgttcca gggtctgttt cc                            32

<210> SEQ ID NO 13
<211> LENGTH: 35
<212> TYPE: DNA
<213> ORGANISM: Artificial Sequence
<220> FEATURE:
<223> OTHER INFORMATION: primer 1 for the construction of the
      recombinant eukaryotic plasmid for expressing the recombinant
      proteins LhFVII, LhFIX, and LhFX

<400> SEQUENCE: 13
taaggatcct gcagagattt catcatggtc tccca                         35

```
<210> SEQ ID NO 14
<211> LENGTH: 40
<212> TYPE: DNA
<213> ORGANISM: Artificial Sequence
<220> FEATURE:
<223> OTHER INFORMATION: primer 2 for the construction of the
      recombinant eukaryotic plasmid for expressing the recombinant
      proteins LhFVII, LhFIX, and LhFX

<400> SEQUENCE: 14
tatctcgagt taatgatgat gatgatgatg tcggccttgg                         40

<210> SEQ ID NO 15
<211> LENGTH: 39
<212> TYPE: DNA
<213> ORGANISM: Artificial Sequence
<220> FEATURE:
<223> OTHER INFORMATION: primer 3 for the construction of the
      recombinant eukaryotic plasmid for expressing the recombinant
      proteins LhFVII, LhFIX, and LhFX

<400> SEQUENCE: 15
taaggatcct gcagagattt catcatgcag cgcgtgaac                          39

<210> SEQ ID NO 16
<211> LENGTH: 41
<212> TYPE: DNA
<213> ORGANISM: Artificial Sequence
<220> FEATURE:
<223> OTHER INFORMATION: primer 4 for the construction of the
      recombinant eukaryotic plasmid for expressing the recombinant
      proteins LhFVII, LhFIX, and LhFX

<400> SEQUENCE: 16
tatctcgagt taatgatgat gatgatgatg acgggtgagc t                       41

<210> SEQ ID NO 17
<211> LENGTH: 36
<212> TYPE: DNA
<213> ORGANISM: Artificial Sequence
<220> FEATURE:
<223> OTHER INFORMATION: primer 5 for the construction of the
      recombinant eukaryotic plasmid for expressing the recombinant
      proteins LhFVII, LhFIX, and LhFX

<400> SEQUENCE: 17
taaggatcct gcagagattt catcatgggg cgccca                             36

<210> SEQ ID NO 18
<211> LENGTH: 38
<212> TYPE: DNA
<213> ORGANISM: Artificial Sequence
<220> FEATURE:
<223> OTHER INFORMATION: primer 6 for the construction of the
      recombinant eukaryotic plasmid for expressing the recombinant
      proteins LhFVII, LhFIX, and LhFX

<400> SEQUENCE: 18
tatctcgagt taatgatgat gatgatgatg gcgttcca                           38
```